United States Patent [19]

Harris

[11] Patent Number: 5,399,371
[45] Date of Patent: Mar. 21, 1995

[54] LOW CALORIE SUBSTITUTE FOR AN EDIBLE OIL

[75] Inventor: Eugene G. Harris, West Chester, Ohio

[73] Assignee: Henkel Corporation, Plymouth Meeting, Pa.

[21] Appl. No.: 79,117

[22] Filed: Jun. 17, 1993

[51] Int. Cl.$^6$ ............................................. A23D 9/00
[52] U.S. Cl. .................................. 426/611; 426/804; 549/378; 549/347
[58] Field of Search ................ 426/611, 804; 549/378, 549/347

[56] References Cited

U.S. PATENT DOCUMENTS 4,005,195  1/1977  Jandacek .......................... 424/180
4,861,613  8/1989  White et al. ....................... 426/611

FOREIGN PATENT DOCUMENTS 0236288  9/1987  European Pat. Off. .
0350988  1/1990  European Pat. Off. .

*Primary Examiner*—Carolyn Paden
*Attorney, Agent, or Firm*—Ernest G. Szoke; Wayne C. Jaeschke; Real J. Grandmaison

[57] ABSTRACT

A polyglycerol composition of the formula

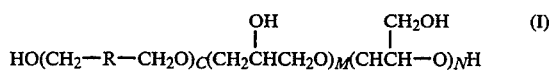

(I)

wherein R may be

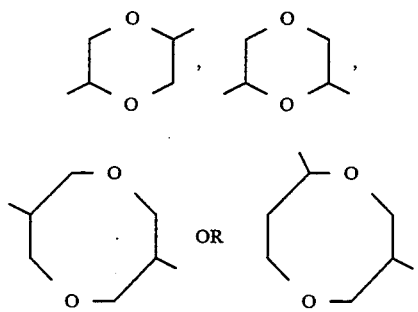

C comprises up to about 3 percent of all N+M units, and N+M is a number from about 3 to about 15, and wherein the polyglycerol is essentially free of low molecular weight glycerides selected from the group consisting of glycerine, diglycerine and triglycerine. The polyglycerol may be esterified to provide a low calorie polyglycerol polyester food composition, or it may be alkoxylated and then esterified to provide a low calorie alkoxylated polyglycerol polyester food composition.

19 Claims, No Drawings

LOW CALORIE SUBSTITUTE FOR AN EDIBLE OIL

BACKGROUND OF THE INVENTION

1. Field of the Invention

This invention relates to a composition of matter and to the process for making such composition which is useful as a low calorie substitute for an edible oil. The low calorie substitute for an edible oil is provided by preparing higher molecular weight polyglycerol polyesters, and alternately, wherein the polyglycerols have been reacted with an epoxide and then esterified.

Presently, one of the most common and difficult problems for people is excessive body weight. This condition is due partly to excessive ingestion of calories and partly to insufficient exercise to expend the calories. The primary source of calories is fat in foods, with each gram of fat supplying about 9 calories. On the whole, fat constitutes about 40% of the total calories in people's diets. Accordingly, in order to reduce the intake of calories, it is necessary that a person reduce one's fat ingestion.

There is certainly adequate motivation for reducing one's calorie intake. Fats have been associated with chronic diseases such as heart disease, cancer and obesity. Therefore, by reducing the intake of fat and the associated calories, many people attempt to also reduce the risk of such afore-mentioned diseases. Besides such physical problems, there are associated psychological problems related to obesity such as poor self-esteem and decreased confidence. Thus, if one's physical appearance is improved, one's mental health is likewise improved. Hence, it would be very beneficial to the general public to replace fatty materials with a food substance having reduced calories.

2. Discussion of Related Art

Recently, a number of fat replacers have been proposed for use in foods. These fat replacers may be divided into two categories, i.e., synthetic fat substitutes and fat mimics. The fat mimetics merely attempt to mimic the mouthfeel of fats. They are carbohydrate and protein based, and as such contain four calories per gram, not the nine calories per gram of fats. They suffer, however, from instabilities to varying degrees and are invariably unstable at frying temperatures. Also, such fat mimetics have not entirely been found acceptable since they do not possess the properties of triglycerides, the main component of natural edible fats and oils. That is, the fat replacer must possess the desirable property of edible fats and oils of being rich in taste and have the textural characteristic associated with a particular food. For example, the rich taste and creamy mouthfeel of ice cream or chocolate is generally attributed to the fat in the food. To have acceptance, a low calorie fat substitute would necessarily have to possess these properties. In addition, such fat substitute should have a color and consistency that is similar to natural edible fats and oils, and if in solid form, should melt smoothly without decomposition to retain the organoleptic properties associated therewith. The organoleptic properties associated with natural edible fats and oils depend upon the fatty acids of the triglycerides. Triglycerides are triesters of glycerine and various fatty acids. The fatty acids may be saturated, unsaturated, cyclic, acylic, oxygenated or non-oxygenated.

In addition, the fat substitute should be oxidatively stable, that is, it should not form color bodies, malodor bodies, nor polymerize any more rapidly than natural fats and oils. Further, the fat substitute should maintain a viscosity close to, and no greater than, that of a natural oil at frying temperatures, for example such as in frying snack foods. The resulting smell, taste and mouthfeel of the fried food must be similar to that of natural edible fats and oils, and not provide a waxy mouthfeel which may be caused by too low or narrow melting point ranges of the fat or oil. These desirable qualities are better attained by the second class of fat replacers, i.e., the fat mimics. These materials try to duplicate the physical characteristics of natural oils.

Another important criteria for a fat substitute is that it not be absorbed by the body when consumed, i.e., it should not be hydrolyzed by pancreatic lipase and thus absorbed through the digestive tract, or if so, only to a minimal extent. In addition, the fat substitute should not cause medical side effects such as diarrhea or anal leakage. Prior art fat substitutes that are not absorbed by the body generally tend to cause diarrhea-like problems when significant amounts thereof are consumed. This problem is said to be overcome by the addition of fats or hardened oils as indicated in U.S. Pat. No. 4,005,195 directed to sucrose polyester fat substitutes, or by providing a more plastic-like oil material as indicated in EP Applications 236,288 and 350,988.

Another type of fat substitute is reported in EP Publication 87 306 468.7 and U.S. Pat. No. 4,861,613 relating to esterified epoxide-extended polyols having the general formula $P(OH)_{a+c}(EPO)_n(RCOOH)_b$, wherein $P(OH)$ is a polyol having 1 to 8 primary hydroxyl groups (a), and c is equal to 0 to 8 secondary plus tertiary hydroxyl groups, with $a+c$ being in the range of 3 to 8 hydroxyls; EPO is a $C_3$-$C_6$ epoxide; and RCOOH is a fatty acid acyl moiety in which R is an alkyl chain of at least 2 carbon atoms. The polyols are treated in the presence of a base catalyst with an epoxide to produce epoxide-extended polyols, which is then reacted with a fatty acid to produce the ester thereof. Every hydroxyl group on the polyol is replaced with an ether linkage. Examination of the '613 Patent does not reveal any reference to polyglycols or polyglycerols, only to glycerols.

Polyglycerol esters have been referred to as fat substitutes in the literature. However, these materials are partially esterified polyglycerols that act as emulsifiers and can give some of the mouthfeel of true fats. These materials are only stable at low temperatures. Also, rat feeding studies, described in the literature, have shown that polyglycerol esters, even those termed decaglycerol dodecaoleate, were substantially absorbed, and would therefore also be in humans.

Accordingly, there exists a need for a low calorie fat material that is effective at reducing calorie retention, that does not taste waxy in the mouth, that is stable at elevated temperatures such as during frying of foods, and that does not produce an undesirable laxative side effect.

DESCRIPTION OF THE INVENTION

Other than in the operating examples, or where otherwise indicated, all numbers expressing quantities of ingredients or reaction conditions used herein are to be understood as modified in all instances by the term "about".

In accordance with this invention, there is provided a composition of matter comprising an edible, wholly or partially nondigestible low calorie fat material comprising a higher molecular weight polyglycerol polyester, and alternately, a higher molecular weight polyglycerol reacted with an epoxide and then esterified with a fatty acid. The aforementioned compositions are useful as a substitute for triglyceride fats in low calorie fat-containing food products. In addition, the compositions may be made from $C_{10}$–$C_{22}$ saturated and unsaturated fatty acids to prevent diarrhea or anal leakage.

By "wholly nondigestible" is meant that substantially all of the low calorie fat material is not digested by the body in that it passes through the digestive system substantially the same as when it was ingested. The term "partially nondigestible" means that at least about 30% of the fat material is not digested, and preferably at least about 70% of the fat material is not digested.

The polyglycerol is made according to the common practice of base-catalyzed dehydration of glycerine at a temperature of between about 240° C. and about 260° C. using an alkali metal salt such as sodium hydroxide or potassium hydroxide. The catalyst can be added all at once at the beginning of the reaction or it can be added in aliquots during the course of the reaction. A nitrogen sparge is preferably maintained during the dehydration step to reduce oxidation. The progress of the reaction can be followed by hydroxyl value, refractive index, gas chromatography, high pressure liquid chromatography, or super critical fluid chromatography. In accordance with this invention, the polyglycerol is then stripped to remove all low molecular weight glycerides such as glycerine, diglycerine and triglycerine by employing suitable means such as a wiped film evaporator to provide a polyglycerol having the following structure as represented by formula I

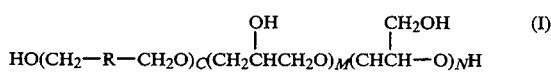

wherein R may be

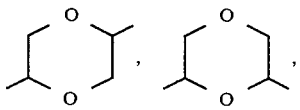

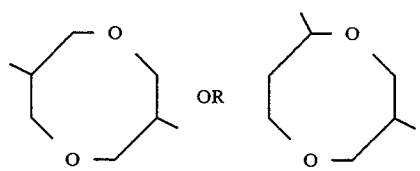

C comprises up to about 3 percent of all N+M units. In formula I, N+M may be from about 3 to about 15, but is preferably from 4 to 12. In the most preferable mode, N+M is about 6 because a higher molecular weight is less easily absorbed by the body, but too high of a molecular weight produces undesirable physical characteristics such as high viscosity. However, the processes that are currently available to produce polyglycerols always produce statistical distributions.

The polyglycerol polyester may also be prepared by transesterification of the polyglycerols with triglycerides with the resulting separation of glycerine and the formation of the required polyglycerol polyester. The triglycerides are in the form of any of the typical edible oils. This may be illustrated by the following reaction:

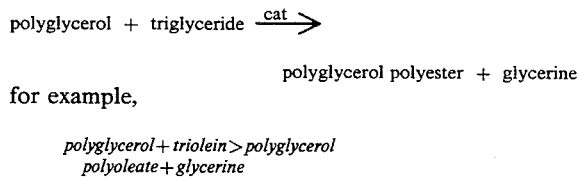

for example,

*polyglycerol + triolein > polyglycerol polyoleate + glycerine*

It has been found that by eliminating essentially all of the polyglycerols with G values of 1 to about 3, the resulting polyglycerol esters are more stable to hydrolysis by pancreatic lipase. By "G value" is meant the number of glycerol units in the glycerol oligomer. The polyglycerol may contain from $G_3$ to $G_{15}$ oligomers, but preferably, contains from $G_4$ to $G_{12}$ oligomers. The polyglycerol is then treated by suitable means, e.g., by ion exchange, to remove the base catalyst, and then treated to remove color bodies such as by carbon filtration. Other well-known bleaching aids such as ion exchange resins and clays may be used.

In one embodiment of this invention, the polyglycerol is then esterified with a fatty acid or derivative thereof to provide a low calorie polyglycerol polyester of this invention having the following structure as represented by formula II.

wherein R, C, N+M are as above with respect to formula I, and R' is a $C_{10}$–$C_{22}$ acyl group derived from aliphatic acids found in typical edible oils.

In another embodiment of this invention, the polyglycerol of formula I is treated with from between about 0.5 to about 4 equivalents of an alkylene oxide per equivalent of hydroxyl in the polyglycerol and then esterified with a fatty acid or derivative thereof to provide an alkoxylated low calorie polyglycerol polyester of this invention having the following structure as represented by formula III:

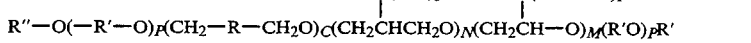

wherein R, C, N+M are as above with respect to formula I, R" is a $C_{10}$–$C_{22}$ acyl group derived from aliphatic acids, and R' is equal to

wherein R''' may be H or $C_1$ to $C_3$, and P may be an integer from 0 to 6.

In each embodiment, after esterification, the product can be extracted, e.g., with methanol, to remove excess acid and the esters treated to remove color such as by filtration.

In another embodiment, the polyglycerol polyester can be stripped of volatile materials by means of a wiped film distillation process. The polyglycerol polyester may be hardened and stabilized by hydrogenation. Further processing may be added that is normal for any food grade triacyl glyceride oil.

The molecular weight of the polyglycerol polyester may be from about 1,010 to about 5,413, but is preferably from about 1,910 to about 4,630 because by producing a polyglycerol having a high molecular weight, the ester derivatives of the polyglycerol are less susceptible to enzymatic hydrolysis and absorption, although a lower molecular weight polyglycerol may be useful in applications where the high molecular weights are not desirous. Additionally, the molecular weight of the polyglycerol will depend on whether a diglycerol, triglycerol, tetraglycerol and the like is produced. The higher molecular weight polyglycerols are preferred for the preparation of the low calorie oil. The molecular weight distribution is also important, since the presence of lower molecular weight and very high molecular weight oligomers may affect the over-all performance of the derived polyglycerol oils as low calorie oils.

In addition, by selection of particular fatty acids in particular proportions, it is possible to control such properties as the melting point, heat stability, as well as viscosity, taste, mouthfeel, color, nondigestibility and anti-anal leakage properties of the polyglycerol polyester. Hydrogenation of a wide variety of oils and fats can also give control of these desirable properties. Such is advantageous in terms of flexibility as to providing a low calorie food substitute having desired physical and chemical properties.

The low calorie food substitute is suitable for replacing fats or oils in many different foods. The low calorie food substitute is useful as a cooking fat or oil, in margarine spreads, in butter, baked articles and baking mixes, confections, frostings, salad dressings, frozen desserts, ice cream, puddings and candies. A common use of fats or oils is in the snack industry for the preparation of food items such as potato chips, corn chips, etc. Since fat or oil is absorbed by foods during frying, a low calorie fat substitute is very useful for producing such food items, thereby producing a low calorie food.

There are many advantages of the process of this invention over known processes practiced in the prior art. For example, no low calorie fat substitute currently available can be used to fry foods, which leaves a large portion of the food industry without a suitable fat substitute, since none of the available prior art fat substitutes are stable at the required frying temperatures. Although there are many so-called fat substitutes available, it is known that many do not duplicate the exact mouthfeel of oil. The polyglycerol polyesters disclosed herein have the necessary mouthfeel because they are structurally and physically very similar to a naturally-occurring oil or fatty acid. Also, the materials disclosed herein have similar odor characteristics as naturally-occurring fats because they are prepared from the fatty acids that are present in these fats and oils.

The fatty acid employed in the esterification of the polyglycerol to produce the polyester can be derived from fatty acids found in typical edible oils such as olive oil, soybean, coconut oil, palm oil, cottonseed oil, and the like. The fatty acids may also include oleic, octanoic, lauric, eicosanoic, stearic, palmitic, linoleic, myristic acid, and linolenic acids or the acyl group may be derived from a complex mixture of these fatty acids. Additionally, the acyl group may be derived from mixtures of natural oils that are short, medium, or long chain, saturated or unsaturated, cis or trans. Examples of short chain acyl groups derived from shorter chain aliphatic acids may include, but are not limited to, valeric, hexanoic, or octanoic acids. Medium chain acyl groups may be derived from, but are not limited to caproic, caprylic, capric, lauroleic, lauric, caproleic and decenoic acid. Long chain acyl groups may be derived from, but are not limited to, behenic, lignoceric, arachidic, myristoleic, palmitoleic, gadoleic, erucic, elaidic, vaccenic, archidonic, and eicosapentaenoic acid. The acyl group is preferably obtained from one or more fatty acid types, and most preferably is obtained from a mixture of the fatty acids that are derived from natural oils and fats.

In the embodiment where the polyglycerol is treated with an alkylene oxide prior to esterification, the alkylene oxide may have 2 to 6 carbon atoms. However, it is preferred that the alkylene oxide have 2 to 3 carbon atoms, i.e., that it comprise ethylene oxide and/or propylene oxide.

In the preparation of the polyglycerol of this invention, the catalyst may be selected from lithium, sodium, rubidium, magnesium, cesium, metal hydroxides such as sodium hydroxide, calcium hydroxide, and barium hydroxide, metal hydrides such as sodium, potassium, lithium, and calcium hydride, lithium aluminum hydride, sodium borohydride, carbonates, sodium amide and sodium sulfate, but preferably it comprises sodium or potassium. The amount of catalyst heated with the glycerine, based on the amount of glycerine employed, is from about 0.001 wt. percent to about 10 wt. percent, preferably about 1 wt. percent to about 5 wt. percent. The quantity of catalyst present affects the color of the resulting polyglycerol, since the more catalyst used, the darker the color of the polyglycerol. Thus, in order to control the color of the polyglycerol and ultimately the low calorie oil, the amount of catalyst used may be adjusted according to the parameters described herein.

Generally, any means of esterifying the polyglycerol is suitable to produce the low calorie fat substitute of this invention. The polyglycerol may be transesterified by using any of the transesterification catalysts known in the art. Examples of such catalysts include organic titanates, organic acids, or mineral acids. Typically, esterification of the polyglycerol is accomplished by stirring the polyglycerol with a catalyst used in esterification processes such as, pyridine, cyclohexyl-carbodiimide, p-toluene sulfonic acid, hypophosphoric acid, and the like, at a temperature of about 15° C. to about 240° C., preferably from about 20° C. to about 220° C. A fatty acid, fatty acyl halide, ester of fatty acid, or a fatty acyl anhydride is added to the polyglycerol mixture, for example, oleic, stearic, palmitic and their anhydrides, halides and methyl esters or mixtures thereof. A solvent may be added at any time, to aid in the proper mixing of the reaction mixture. If a solvent is added, any nonpolar, aprotic solvent may be used. However, hydrocarbon solvents, such as hexane, are preferred.

The resulting crude low calorie oil can be filtered and extracted with any number of polar solvents. Water, ethanol, methanol, isopropanol or any combination of these is preferred. Salts such as sodium chloride, potassium chloride and the like, or alkaline materials such as sodium hydroxide, potassium hydroxide and the like may be added to-the aqueous extracting phase to aid in extraction of free fatty acids and separation of phases. The solvent may be removed from the oil by a number of means, but is done most conveniently using a rotary evaporator. The oil can be deodorized if desired by steam stripping or treated further in any manner that normal oils are treated. Additives may or may not be added, as deemed desirable.

In a preferred embodiment, the polyglycerol is reacted with an alkylene oxide under alkaline conditions. The alkylene oxide preferably comprises ethylene oxide and/or propylene oxide. Such reaction causes the primary hydroxyls present to become secondary or tertiary hydroxyls which is desirable because it is believed that the product is then less easily digested by enzymes and, thus, not absorbed by animals and humans. In the reaction of the polyglycerol with the alkylene oxide, the polyglycerol is stirred with a catalyst, preferably as nitrogen is flushed through the system. The catalyst is similar to the catalyst used herein to make the polyglycerol. The temperature is gradually raised from about 20° C. to about 150° C., preferably about 20° to about 140° C., then the alkylene oxide is slowly added to the polyglycerol and reacted until the alkylene oxide vapor pressure ceases to drop. After reacting the polyglycerol with the alkylene oxide, the resulting compound can be esterified as previously described herein to form the low calorie oil. The reacted crude oil can be further processed or purified if so desired, such as by the procedures discussed herein for unreacted crude oils.

The ratio of polyglycerol to alkylene oxide will depend on the hydroxyl value. It is preferable to use 1:05 to 1:6 equivalents of hydroxyl to propylene oxide, and more preferably to use 1:1 to 1:4 equivalents.

When the low calorie oil is fed to animals, a high percentage of the low calorie oil is recovered in animal feces after animal digestion, i.e., at least 50 percent is recovered, preferably 60 to 100 percent is recovered, and more preferably 70 to 100 percent is recovered.

The following examples further illustrate and describe the present invention, but are not intended to be limitations thereof.

EXAMPLE I

A polyglycerol was prepared in the following manner. Glycerine was charged to a reaction vessel along with 2 weight % of sodium hydroxide. The vessel was supplied with a mechanical stirrer, a means to ascertain the temperature of the vessel contents, subsurface nitrogen sparge and a short column equipped with a condenser and receiver to collect the water eliminated during the reaction. The reaction vessel was maintained between 240° and 260° C. during the condensation and a nitrogen sparge was maintained while the glycerine or polyglycerol was heated.

The course of the reaction was followed by hydroxyl value and measurement of the amount of collected water. When the appropriate endpoint was reached, the resulting polyglycerol was cooled to 100° C., diluted with water to a 50% solution and run through a cation exchange column to remove the catalyst. After removing the water of dilution, the crude polyglycerol was then passed through a wiped film stripping unit to remove residual glycerine and low molecular weight polyglycerines. The barrel of the wiped film unit was maintained at 260° C. and the pressure was held between 10 and 50 milli Torr.

The polyglycerol, after stripping on the wiped film evaporator, was made up of oligomers that range between $G_4$ and $G_{12}$. A gas chromatography analysis of the trimethyl silyl derivatives indicate the polyglycerol to have the following typical oligomer distribution.

| | | | |
|---|---|---|---|
| $G_3$ | 1.2 | $G_8$ | 10.9 |
| $G_4$ | 11.7 | $G_9$ | 8.4 |
| $G_5$ | 18.0 | $G_{10}$ | 7.4 |
| $G_6$ | 16.5 | $G_{11}$ | 6.3 |
| $G_7$ | 13.3 | $G_{12+}$ | 6.2 |

Analysis by proton NMR of the polyglycerol acetates, prepared by treatment with acetic anhydride, shows the secondary to primary hydroxyl ratio to be about 1 to 1.

The polyglycerol was diluted to a 50% aqueous solution and mixed with 1% by weight of Darco KB carbon, based on the weight of the polyglycerol.

The suspension was heated to 60° C. and held at that temperature for 8 hours. The suspension was then cooled and allowed to settle overnight. The suspension was then filtered through a filter aid to yield a nearly colorless, clear solution. Water was then stripped from the polyglycerol.

The acid value (AV) of the polyglycerol was 4.2 and the hyroxyl value was 862.

EXAMPLE II

A polyglycerol formed as in Example I was reacted with propylene oxide in the following manner. Polyglycerol, 509 parts, was charged to a Parr pressure reactor. Sodium hydride, 1.8 parts, was added under nitrogen. The reactor was sparged with nitrogen and warmed to 145° C. Propylene oxide, 566 parts, was added over a 19-hour period. The reaction temperature was maintained between 145° and 160° C. and the pressure was held between zero and sixty psig. The product was diluted to a 50% solution with water and deionized. The deionized product was stripped of water and passed through a Pope wiped film still. The barrel temperature was maintained at 250° C. and the pressure was held at 40 to 60 milli torr. The yield was 921 parts. A second batch was prepared in a like manner. The two batches were combined and had a hydroxyl value of 456 and had 88% secondary hydroxyls, as determined by proton NMR.

EXAMPLE III

The polyglycerol prepared in Example I was esterified with oleic acid having the following composition.

| | | | |
|---|---|---|---|
| $C_8$ | | $C_{16:1}$ | 4.8 |
| $C_{10}$ | | D | 0.6 |
| A | | $C_{17}$ | 0.16 |
| $C_{12}$ | | $C_{17:1}$ | 1.0 |
| $C_{14}$ | 1.3 | $C_{18}$ | 0.71 |
| $C_{14:1}$ | −.33 | $C_{18:1}$ | 74.5 |
| A | −.22 | $C_{18:2}$ | 10.3 |
| B | | $C_{18:3}$ | 0.6 |
| $C_{15}$ | 0.14 | D | 0.4 |
| BB | | $C_{20:1}$ | 0.7 |
| $C_{16}$ | 3.8 | BB | 0.2 |

Oleic acid, 3016 parts; polyglycerol, 500 parts; Darco KB carbon, 3.5 parts; and hypophosphorous acid, 1 part, were placed in a flask equipped with a stirrer, pot thermometer, $N_2$ subsurface sparge, Vigreaux column and Dean Stark trap plus condenser. After 9 hours at 215° C., a vacuum of 10 mm Hg was applied and held for one hour at 210° C. A hydroxyl value of 3.5 showed that esterification was complete. The acid value at this point was 18.9. After filtration through perlite to remove carbon, the crude product was passed through a 4-inch barrel wiped film evaporator to remove excess oleic acid. The barrel temperature was held at 250° C. and the vacuum held at 20 microns. The feed rate was approximately 1 kg/hour. Yield of polyglycerol polyoleate was 2300 parts.

The polyglycerol polyoleate had the following physical parameters:

| | |
|---|---|
| Acid value (AV) = | 0.25 |
| Iodine value (IV) = | 80.4 |
| Hydroxyl value (OH) = | 2.88 |
| Sap. value = | 176.4 |
| Viscosity (in centipoise) at 25° C. = | 309 |
| Density at 15° C. = | 0.9417 |

EXAMPLE IV

The polyglycerol that was reacted with propylene oxide in Example II was esterified with oleic acid (see Example III for analysis of oleic acid) in the following way. Propoxylated polyglycerol, 800 parts; oleic acid, 2750 parts; Darco KB carbon, 3.5 parts; and hypophosphorous acid, 1.6 parts, were placed in a flask equipped with a thermometer, Dean Stark trap/condenser, stir bar, subsurface nitrogen sparge, and heating mantel with controller. The pot contents were maintained at 210°–220° C. for eight hours. At this point, water collection stopped. The Dean Stark trap was then replaced with an eight-inch Vigreaux column and condenser/receiver. A vacuum of 10 mm Hg was applied and held for two hours. Then a vacuum of .5 to 1 mm Hg was applied to remove excess oleic acid. When the oleic acid stripping stopped, the pot contents were cooled and filtered through perlite. The acid value was 19.5 and the hydroxyl value was 4.9.

The product was then run through a Pope 4-inch wiped film evaporator with the barrel held at 260° C., the vacuum held at 20–40 microns and the feed rate approximately 1 kg/hour. The yield was 2010 parts. The analysis of the product was as follows:

| | |
|---|---|
| Acid value (AV) | 0.35 |
| Hydroxyl value (OH) | 0.68 |
| Sap. value | 142.0 |
| Iodine value (IV) | 63.5 |
| Viscosity (in centipoise) at 25° C. | 469 |
| Density at 15° C. | 0.9538 |

EXAMPLE V

The propoxylated polyglycerol prepared in Example II was esterified with food grade tallow fatty acids having the following compositions:

| Components | Area % |
|---|---|
| $C_{12}$ | 0.20 |
| $C_{14}$ | 3.5 |
| 14:1 | 0.69 |
| $C_{15}$ | 0.55 |
| $C_{16}$ | 25.5 |
| 16:1 | 3.2 |
| UNK A | 0.82 |
| $C_{17}$ | 1.4 |
| 17:1 | 0.84 |
| $C_{18}$ | 16.0 |
| 18:1 | 41.6 |
| 18:2 | 2.8 |
| 18:3 | 0.17 |

| Components | Area % |
|---|---|
| UNK B | 0.59 |
| Others | 2.1 |

Propoxylated polyglycerol, 795.3 parts; tallow fatty acids, 2192.6 parts; Darco KB carbon, 3.0 parts; and hypophosphorous acid, 1.6 parts, were placed in a reaction vessel equipped with a pot thermometer, stirrer, subsurface nitrogen sparge, and a Dean Stark trap/condenser. The reaction mixture was held at 215° C. until water stopped collecting. A vacuum of 10 mm Hg was then applied for two hours, which was increased to 1 mm Hg to strip excess tallow acids. After stripping, the product was cooled to 60° C. and filtered through perlite 476. The acid value was 11.6 and the hydroxyl value was 3.6. The polyglycerol tallowate ester was then passed through a Pope 4-inch wiped film evaporator. The acid value after stripping excess tallow fatty acids was 0.33. The yield was 1988 parts. Some of this product was then hydrogenated to create a highly saturated, low oleic, polyglycerol polyester. Palladium on alumina, 1.5 parts of a 5% dispersion, was added to 1500 parts of the high iodine value material in a 2 L Parr autoclave. After sparging with nitrogen, the autoclave was heated to 205° C., pressurized with hydrogen to 300 psig, and reacted for one hour. The autoclave was then cooled and the remaining pressure was released.

The filtered product had the following physical attributes:

| | |
|---|---|
| Acid Value | 0.4 |
| Hydroxyl Value | 3.6 |
| Iodine Value | 4.3 |
| Sap. Value | 143.2 |
| Peroxide Value | .57 |
| Color (Gardner) | 2+ |

EXAMPLE VI

Preparation of a Polyglycerol Polyester From a Typical Commercially Available Decaglycerol A sample of Mazor decaglycerol tetraoleate was split and analyzed to determine the composition of the polyglycerol backbone. After preparation of a trimethyl silyl derivative, the polyglycerol was analyzed by gas chromatography. The following analysis indicated free glycerine, diglycerols and triglycerols to be present:

| | |
|---|---|
| $G_1$ | 2.5 |
| $G_2$ | 25.1 |
| $G_3$ | 23.5 |
| $G_4$ | 13.0 |
| $G_5$ | 10.1 |
| $G_6$ | 7.9 |
| $G_7$ | 6.3 |
| $G_8$ | 4.6 |
| $G_9$ | 3.0 |
| $G_{10+}$ | 4.0 |

The decaglycerol tetraoleate, 688 parts; oleic acid (see Example III for analysis), 900 parts; and hypophosphorous acid, 2 parts; were placed in a flask equipped with a stirrer, pot thermometer, $N_2$ subsurface sparge, Vigreaux column with Dean Stark trap and condenser. After 11 hours at 210° C., a vacuum of 10 mm Hg was applied for four hours. A vacuum of 1 mm Hg was then applied and excess oleic acid was stripped. The product was then placed on a continuous liquid-liquid extractor and run for two days using methanol as the solvent. The methanol was then stripped from the product, which had the following physical properties:

| | |
|---|---|
| Acid Value | 0.19 |
| Hydroxyl Value | 6.5 |
| Sap. Value | 177 |
| Iodine Value | 80.3 |
| Viscosity in centipoise @ 25° C. | 235 |

EXAMPLE VII

Preparation of a Polyglycerol Polyoleate From a Polyglycerol Containing $G_2$ and $G_3$ Polyglycerols A polyglycerol was prepared in accordance with the method disclosed in Example I except that the Pope wiped film barrel temperature was set at 210°–220° C. The polyglycerol had the following composition:

| Glycerine | Area % |
|---|---|
| $G_1$* | .47 |
| $G_2$* | 5.85 |
| $G_3$* | 17.55 |
| $G_4$* | 18.54 |
| $G_5$* | 15.77 |
| $G_6$* | 12.62 |
| $G_7$* | 9.73 |
| $G_8$* | 7.66 |
| $G_9$* | 5.95 |
| $G_{10}$* | 3.81 |
| $G_{11+}$* | 1.87+ |

*Combination of isomers
Hydroxyl Value = 918
Secondary Hydroxyls = 53.7%, by proton NMR Polyglycerol, 200 parts; oleic acid, 1097 parts; and hypophosphorous acid, 0.3 parts; were placed in a vessel equipped with a stirrer, pot thermometer, $N_2$ sparge, and Dean Stark trap with condenser. After 5 hours at 200° C., the temperature was increased to 215° C. and a vacuum of 0.5 mm Hg was applied. When the excess oleic acid was stripped, 32 parts of Filtrol Grade I was added at ambient temperature. The product was taken to 90°–100° C. and held for 1 hour, and then filtered through dicalite. After filtration, the product was extracted on a continuous liquid-liquid unit for 16 hours with methanol. After stripping excess entrained methanol, the polyglycerol polyester had the following physical properties:

| | |
|---|---|
| Acid Value | 0.12 |
| Hydroxyl Value | 10 |
| Sap. Value | 175.6 |
| Viscosity (in centipoise) @ 25° C. | 253 |

EXAMPLE VIII

A polyglycerol was prepared according to the method of Example I. This polyglycerol then had the following composition:

| | |
|---|---|
| $G_1$–$G_2$ | 1.55 |
| $G_3$ | 7.21 |
| $G_4$ | 15.29 |
| $G_5$ | 16.38 |
| $G_6$ | 10.91 |
| $G_7$ | 10.90 |
| $G_8$ | 11.65 |
| $G_9$ | 7.16 |
| $G_{10}$ | 6.46 |
| $G_{11}$ | 5.50 |
| $G_{12}$ | 6.87 |

The polyglycerol had a hydroxyl value of 858.

EXAMPLE IX (Part of VIII)

Part of the polyglycerol of Example VIII was propoxylated according to the method described in Example II except that the ratio of propylene oxide to hydroxide equivalent was 0.75:1. The finished propoxylated polyglycerol then contained 75% secondary hydroxyls as detected by proton NMR. Gas chromatography showed that all of the oligomers of the original polyglycerol had been propoxylated.

EXAMPLE X

The propoxylated polyglycerol of Example IX, 490 parts; oleic acid, 2796 parts; and hypophosphorous acid, 1 part; were reacted and the product purified as described in Example VI.

The product had the following physical characteristics:

| | |
|---|---|
| Acid Value | 0.3 |
| Hydroxyl Value | 3.4 |
| Iodine Value | 72.0 |
| Peroxide Value | 2.4 |
| Sap. Value | 156.3 |
| Viscosity (in centipoise) @ 25° C. | 373 |

EXAMPLE XI

Another portion of the polyglycerol of Example VIII, 410 parts; oleic acid, 2386 parts; and hypophosphorous acid, 1 part; were reacted according to the method described in Example IV. After the excess oleic acid was stripped, the acid value was 21.

The residual acid was then removed on a continuous liquid-liquid extractor using methanol as the extractant. The polyglycerol polyester then had the following physical characteristics:

| | |
|---|---|
| Acid Value | 0.3 |
| Hydroxyl Value | 3.2 |
| Iodine Value | 79.6 |
| Peroxide Value | 6.4 |
| Sap. Value | 179.3 |
| Viscosity (in centipoise) @ 25° C. | 294.7 |
| Density at 25° C. | .9412 |

EXAMPLE XII

Lipase Testing

The polyglycerols in Examples III, IV, V, VI, VII, X, XI were subjected to digestion by porcine pancreatic lipase to test for resistance to hydrolysis. This test is an indicator of resistance to digestion within a mammalian digestive system.

Lipase Assay—The following materials and procedure were employed:

0.05M Tris-HCl buffered at pH=8.0 at 37° C.
3.027 g Tris

Adjust volume to 500 ml
Adjust temperature to 37° C. and adjust pH to 8.0 with conc. HCl.
Salts Solution
  3.8 g NaCl
  0.24 g CaCl$_2$
  200 ml of 0.05M Tris-HCl, pH=8.0 at 37° C. (the above solution).
Histidine Solution
  35 mg L-histidine to 10 ml of 0.05M Tris-HCl, pH=8.0.
Enzyme Solution
  60 mg porcine pancreatic lipase (Sigma Cat. No. L3126) to 5.0 ml of the above L-histidine solution.
Olive oil is used as a standard in these assays. The olive oil is from Sigma, cataloque number 01500.

1. Weigh 0.2000 grams of standard or sample into each of three 125 ml Erlenmeyer flasks.
2. To each flask add 8.0 ml of Salts solution, and 1.0 ml of the 0.05M Tris-HCl solution. Stopper each flask and place them in a shaker water bath equilibrated to 37° C. Commence agitation at 250 rpm. A New Brunswick shaker water bath was used throughout this study.
3. After the samples have equilibrated to temperature, 15-20 minutes, add 1.0 ml of enzyme to each of two flasks and 1.0 ml of histidine solution to the third flask as a blank. Stagger the addition to each flask by at least 30 seconds. The third flask in each set is the sample blank, which accounts for any free acids in the sample. Reactions should run both for 1 hour and 18 hours.
4. When reaction time has expired, add 50 ml of isopropanol to each flask. Prior to titration with 0.05–0.10N KOH in methanol, add a few drops of 1% phenolphthalein in ethanol to each flask. The exact concentration of the potassium hydroxide solution should be standardized using KHP, potassium hydrogen phthalate. Titrate each flask to the pink endpoint and record the amount of base required to neutralize the sample. If solubility is a problem, warm sample slightly in a water bath prior to titration.
5. For olive oil, the % hydrolysis for each sample will be the mmoles KOH divided by the mmoles fatty acids available×(times) 100. An average molecular weight for olive oil of 880 g/mole can be used The corrected % hydrolysis is the % hydrolysis for the lipase-treated sample minus the % hydrolysis for the blank. For more heterogeneous samples (complex esters), the % hydrolysis can be calculated as the (AV/SAP Value)×100. The AV for each sample is (mmole KOH sample—mmole KOH blank) (56 mg KOH/mmole)/sample weight in grams. The saponification value can be determined using a method such as A.O.C.S. Official Method Cd 3-25. It is defined as the mg KOH required to saponify a gram of sample. The % hydrolysis can then be determined by taking a ratio of the measured AV after lipase treatment/SAP VALUE 100.

TABLE I

Results of Lipase Assay

| Sample | Percent Hydrolysis | |
|---|---|---|
| | 1 hr. | 18 hrs. |
| Standard (olive oil) | 55 | 89 |
| Polyglycerol polyoleate of Example III | 2.7 | 4.4 |
| Propoxylated polyglycerol polyoleate of Example IV | 2.7 | 2.3 |
| Propoxylated polyglycerol polytallowate of Example V | 2.4 | 3.8 |

TABLE I-continued

Results of Lipase Assay

| Sample | Percent Hydrolysis | |
|---|---|---|
| | 1 hr. | 18 hrs. |
| Polyglycerol polyoleate from commercial "decaglycerol" of Example VI | 9.2 | 18.8 |
| Polyglycerol polyoleate from Example VII | 4.2 | 7.8 |
| Propoxylated polyglycerol polyoleate from Example X | 2.1 | 4.3 |
| Polyglycerol polyoleate of Example XI | 0.5 | 5.3 |

Discussion of results of lipase test. It has been determined that the lipase assay does not give false positive results, that is, a compound that is hydrolyzed to a degree greater than about 10% by lipase within 24 hours will be absorbed in the mammalian digestive system to an extent of about 70% or greater, and most likely, completely absorbed.

Examination of the above data shows that the polyglycerol polyesters with oligomers in the range of $G_4$ to $G_{12}$ and especially alkoxylated polyglycerol polyesters in the oligomer range of $G_4$ to $G_{12}$ are much more resistant to hydrolysis by pancreatic lipase than the polyglycerol polyesters that contain substantial amounts of $G_1$–$G_3$ oligomers. In particular, the decaglycerol commonly available and used in previous animal studies contains over 50% of the $G_1$ to $G_3$ oligomers. The results of these earlier studies were said to prove that "completely esterified decaglycerol esters were completely hydrolyzed and metabolized in rat feeding studies."

EXAMPLE XIII

TABLE II

Feeding Studies Results

| Material | % Digested in Rats |
|---|---|
| Polyglycerol polyoleate of Example VII | 70 |
| Polyglycerol polyoleate of Example XI | 50 |
| Polyglycerol polyoleate of Example III | 52 |
| Propoxy-capped polyglycerol of Example X | 22 |
| Propoxy-capped polyglycerol oleate of Example IV | 26 |
| Propoxy-capped polyglycerol tallowate of Example V | 18 |

The following conclusions were made from this study. A chain length greater than three polyglycerol units, and propylene oxide capping strongly influenced the absorption of oligopolyglycerol compounds. As the amount of fully esterified higher oligopolyglycerols increases, absorption decreases. Adding at least one-half equivalent of propoxide per hydroxyl function decreases absorption.

No gross toxicity was noted for fully-esterified capped or uncapped polyglycerol esters.

What is claimed is:
1. A low calorie food composition comprising a polyglycerol polyester obtained by esterifying a polyglycerol composition having the structure of formula I

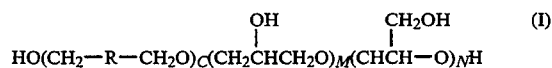

wherein R may be

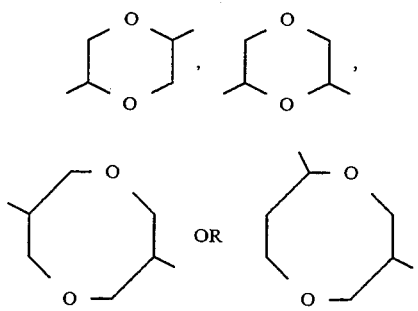

C comprises up to about 3 percent of all N+M units, and N+M is a number from about 3 to about 15, said polyglycerol being essentially free of low molecular weight glycerides selected from the group consisting of glycerine, diglycerine and triglycerine, said polyglycerol polyester having the structure as represented by formula II

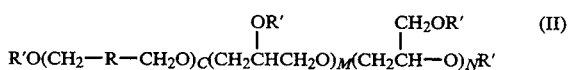

wherein R, C, N+M are as in formula I, and R' is a $C_{10}$–$C_{22}$ acyl group derived from aliphatic acids found in typical edible oils.

2. A low calorie food composition as in claim 1 wherein N+M is a number from about 4 to about 12.

3. A low calorie food composition as in claim 1 wherein said polyglycerol polyester has been hydrogenated.

4. A low calorie food composition as in claim 1 wherein said polyglycerol has been esterified with a fatty acid or fatty acid derivative.

5. A low calorie food composition as in claim 4 wherein said fatty acid comprises an edible oil.

6. A low calorie food composition as in claim 1 wherein said polyglycerol has been treated with from about 0.5 to about 4 equivalents of an alkylene oxide per equivalent of hydroxyl in the polyglycerol, and then esterified with a fatty acid, fatty acyl halide, ester of fatty acid, or fatty acyl anhydride to provide an alkoxylated polyglycerol polyester having the structure as represented by formula III

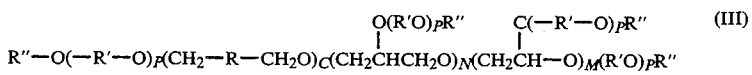

wherein R, C, N+M are as in formula I, R" is a $C_{10}$–$C_{22}$ acyl group derived from aliphatic acids, and R' is equal to

wherein R''' may be H or $C_1$ to $C_3$, and P may be an integer from 0 to 6.

7. A low calorie food composition as in claim 6 wherein said alkylene oxide contains from 2 to 6 carbon atoms.

8. A low calorie food composition as in claim 6 wherein said alkylene oxide is selected from ethylene oxide and propylene oxide.

9. The process of preparing a low calorie food product comprising adding to said product a polyglycerol polyester obtained by esterifying a polyglycerol composition having the structure of formula I

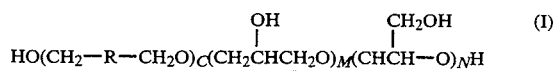

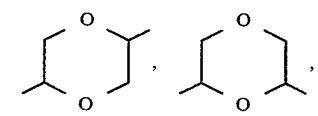

C comprises up to about 3 percent of all N+M units, and N+M is a number from about 3 to about 15, said polyglycerol being essentially free of low molecular weight glycerides selected from the group consisting of glycerine, diglycerine and triglycerine, said polyglycerol polyester having the structure as represented by formula II

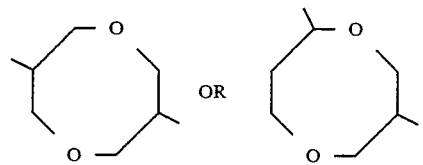

wherein R, C, N+M are as in formula I, and R' is a $C_{10}$–$C_{22}$ acyl group derived from aliphatic acids found in typical edible oils 10. A process as in claim 9 wherein N+M is a number from about 4 to about 12.

11. A process as in claim 9 wherein said polyglycerol polyester has been hydrogenated.

12. A process as in claim 9 wherein said polyglycerol has been esterified with a fatty acid or fatty acid derivative.

13. A process as in claim 12 wherein said fatty acid comprises an edible oil.

14. A process as in claim 9 wherein said polyglycerol has been treated with from about 0.5 to about 4 equivalents of an alkylene oxide per equivalent of hydroxyl in the polyglycerol, and then esteriliad with a fatty acid, fatty acyl halide, ester of fatty acid, or fatty acyl anhydride to provide an alkoxylated polyglycerol polyester having the structure as represented by formula III

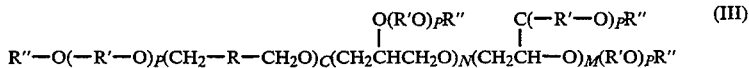 (III)

wherein R, C, N+H are as in formula I, R″ is a $C_{10}$-$C_{22}$ acyl group derived from aliphatic acids, and R′ is equal to

wherein R‴ may be H or $C_1$ to $C_3$, and P may be an integer from 0 to 6.

15. A process as in claim 14 wherein said alkylene oxide contains from 2 to 6 carbon atoms.

16. A process as in claim 14 wherein said alkylene oxide is selected from ethylene oxide and propylene oxide.

17. A process as in claim 9 wherein said polyglycerol has been prepared by dehydrating glycerins with a base catalyst at a temperature of between about 240° C and about 260° C., and removing from the polyglycerol essentially all low molecular weight glycerides selected from the group consisting of glycerine, diglycerine and triglycerine.

18. A process as in claim 17 including maintaining a nitrogen sparge in the reaction vessel during said dehydrating step.

19. A process as in claim 17 including removing the base catalyst from said polyglycerol, treating the polyglycerol to remove color bodies therefrom, and then esterifying the polyglycerol with a fatty acid, fatty acyl halide, ester of fatty acid, or fatty acyl anhydride to provide a polyglycerol polyester composition having the structure of formula II.

* * * * *

UNITED STATES PATENT AND TRADEMARK OFFICE
CERTIFICATE OF CORRECTION

PATENT NO. : 5,399,371
DATED : Mar. 21, 1995
INVENTOR(S) : Eugene G. Harris

It is certified that error appears in the above-indentified patent and that said Letters Patent is hereby corrected as shown below:

In col. 16, line 10 , immediately before ring structures, insert --wherein R may be--, as in claim 1.

In col. 16, claim 14, line 65, delete [esteriliad] and insert --esterified--.

Signed and Sealed this

Third Day of September, 1996

Attest:

BRUCE LEHMAN

Attesting Officer

Commissioner of Patents and Trademarks